United States Patent
Hassell, Jr. et al.

(10) Patent No.: US 10,067,091 B2
(45) Date of Patent: Sep. 4, 2018

(54) INTEGRATED SEDIMENT AND WATER ANALYSIS DEVICE AND METHOD

(71) Applicant: Saudi Arabian Oil Company, Dhahran (SA)

(72) Inventors: James Clyde Hassell, Jr., Dhahran (SA); Luis Gustavo Do Val, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 36 days.

(21) Appl. No.: 15/224,136

(22) Filed: Jul. 29, 2016

(65) Prior Publication Data

US 2018/0031524 A1 Feb. 1, 2018

(51) Int. Cl.
| | |
|---|---|
| *G01N 29/02* | (2006.01) |
| *G01N 15/04* | (2006.01) |
| *G01N 33/28* | (2006.01) |
| *G01N 15/00* | (2006.01) |

(52) U.S. Cl.
CPC ............. *G01N 29/02* (2013.01); *G01N 15/04* (2013.01); *G01N 33/2847* (2013.01); *G01N 2015/0053* (2013.01); *G01N 2291/02416* (2013.01)

(58) Field of Classification Search
CPC .... G01N 29/02; G01N 15/04; G01N 33/2847; G01N 2015/0053; G01N 2291/02416
See application file for complete search history.

(56) References Cited

U.S. PATENT DOCUMENTS

| | | | |
|---|---|---|---|
| 2,928,775 A | 3/1960 | Leisey | |
| 3,528,775 A | 9/1970 | O'Hara et al. | |
| 4,916,077 A | 4/1990 | Forster et al. | |
| 5,340,541 A * | 8/1994 | Jackson | G01N 31/168 205/788 |
| 5,685,192 A | 11/1997 | Shriner et al. | |
| 7,407,625 B1 | 8/2008 | Scott | |
| 7,851,712 B2 | 12/2010 | Luchinger | |
| 7,927,857 B2 | 4/2011 | Nielsen et al. | |
| 8,068,218 B2 | 11/2011 | Higgins et al. | |
| 8,312,757 B2 | 11/2012 | Steinrisser et al. | |
| 2014/0001057 A1 | 1/2014 | Kurose et al. | |
| 2014/0238116 A1 | 8/2014 | Kwan et al. | |

FOREIGN PATENT DOCUMENTS

| | | |
|---|---|---|
| EP | 1715323 A1 | 10/2006 |
| EP | 2419706 B1 | 8/2015 |

OTHER PUBLICATIONS

International Search Report and Written Opinion issued in International Application No. PCT/US2017/042083 dated Nov. 27, 2017; 11 pages.

Mohajer, "Determining Moisture Content in Crude Oil: Karl Fischer vs. Distillation vs. Centrifuge," published on or before Jul. 2015, 3 pages.

* cited by examiner

*Primary Examiner* — Hezron E Williams
*Assistant Examiner* — David Z Huang
(74) *Attorney, Agent, or Firm* — Fish & Richardson P.C.

(57) ABSTRACT

Provided herein are methods and devices for determining water and sediment content in a hydrocarbon fluid sample. The methods and devices for determining water and sediment content in a hydrocarbon fluid sample include a Karl Fischer titration device and a titration vessel configured to implement a Karl Fischer titration and an ultrasonic particle detector configured to identify sediment in the hydrocarbon fluid sample.

26 Claims, 8 Drawing Sheets

FIG. 5A Injection Cap with Septum

FIG. 5B Indicator Electrode

FIG. 5C Generator Electrode and Drying Port

FIG. 5D Solvent Fill and Waste Line

FIG. 5E Insertion Mixer

FIG. 5F Ultrasonic Particle Detector

FIG. 6

Side cut view Probe Collar - Assembly

INTEGRATED SEDIMENT AND WATER ANALYSIS DEVICE AND METHOD

TECHNICAL FIELD

This disclosure relates to analyzing water and sediment in fluid samples, such as hydrocarbon fluid samples.

BACKGROUND

Sediment and water determination in crude oil is sometimes recognized using American Petroleum Institute (API) Manual of Petroleum Measurement Standards (MPMS) 10.4, "Determination of Sediment and Water in Crude Oil by the Centrifuge Method." This method has the advantage of providing both sediment and water volume analyses in one test. However, the method also states it does not provide the most accurate results. Both API and American Society for Testing and Material (ASTM) recommend that when higher degrees of accuracy are required, such as in custody transfer measurement, water determination by distillation (ASTM D4006) or by Karl Fischer titration (ASTM D4377) are used in conjunction with testing sediment in crude oils by extraction (ASTM D473).

SUMMARY

This disclosure describes integrated sediment and water analysis devices and methods for using the same.

Provided herein is a method for determining water and sediment content in a hydrocarbon fluid sample. The method includes integrating a weigh scale with a Karl Fischer titration device and a titration vessel configured to implement a Karl Fischer titration method; integrating an ultrasonic particle detector with the Karl Fischer titration device, the ultrasonic particle detector configured to identify sediment in the hydrocarbon fluid sample; determining, by the weigh scale, the weight of the hydrocarbon fluid sample; performing, by the Karl Fischer titration device, the Karl Fischer titration method on the hydrocarbon fluid sample to determine the water content in the hydrocarbon fluid sample; and identifying, by the ultrasonic particle detector, the sediment content in the hydrocarbon fluid sample.

The Karl Fischer titration device can include a generation electrode for generating $I_2$ and an indicator electrode for measuring electrical current. The generation electrode can extend at least partially into the titration vessel. The indicator electrode can extend at least partially into the titration vessel. The Karl Fischer titration can be performed using the generation electrode and indicator electrode.

In some embodiments, the titration vessel includes a lid. The lid can include a surface that defines a first aperture, a second aperture, and a third aperture. The generator electrode for generating $I_2$ can extend at least partially into the titration vessel through the first aperture. The indicator electrode for measuring electrical current can extend at least partially into the vessel through the second aperture. The ultrasonic particle detector for identifying sediment can extend at least partially into the titration vessel through the third aperture.

The lid can further include an injection cap that includes a septum and the method can further include injecting the hydrocarbon sample into the titration vessel through the septum of the injection cap.

The surface of the lid can further define a fourth aperture. An insertion mixer can extend at least partially into the titration vessel through the fourth aperture. The insertion mixer can mix the hydrocarbon fluid.

The surface of the lid can further define a fifth aperture. A solvent fill line and a solvent waste line can extend at least partially into the titration vessel through the fifth aperture.

In some embodiments, the first aperture is surrounded by a first probe seal that includes a material that is essentially frictionless with regard to the generator electrode. The second aperture can also be surrounded by a second probe seal that includes a material that is essentially frictionless with regard to the indicator electrode. The third aperture can also be surrounded by a third probe seal that includes a material that is essentially frictionless with regard to the ultrasonic particle detector. These seals can permit the generator electrode, indicator electrode, and ultrasonic particle detector to move vertically relative to the vessel. In some embodiments, the first, second, and third probe seals are ferrofluidic seals.

The method can further include enclosing the weigh scale, Karl Fischer titration device, titration vessel, and ultrasonic particle detector within a housing support unit. The top surface of the housing support unit can define a first, second, and third aperture that correspond to the first, second, and third apertures of the titration vessel, respectively, and the generator electrode, indicator electrode, and ultrasonic particle detector can extend at least partially through the corresponding first, second, and third apertures of the housing support unit. The top surface of housing support unit can further define a fourth aperture that corresponds to the fourth aperture of the titration vessel. The insertion mixer can extend at least partially through the fourth aperture of the top surface of the housing support unit. The top surface of housing support unit can further define a fifth aperture that corresponds to the fifth aperture of the titration vessel. The insertion mixer can extend at least partially through the fifth aperture of the top surface of the housing support unit.

In some embodiments, the method further includes decreasing the atmospheric moisture in the housing support unit by integrating a desiccant with the housing support unit.

In some embodiments, the weigh scale is an analytical balance. The Karl Fischer titration can be a coulometric titration. The anode solution can be contained in the titration vessel. The cathode solution can be contained within the generator electrode. A solvent can also be contained in the titration vessel. The solvent can include a diethylene glycol monoethyl ether, chloroform, toluene, xylene, and combinations thereof.

Also provided herein is a method for determining water and sediment content in a hydrocarbon fluid sample using an integrated Karl Fischer-ultrasonic particle detector device (KF-UPD device). The KF-UPD device includes a weigh scale, a Karl Fischer titration device, a titration vessel, and an ultrasonic particle detector. The titration vessel is in contact with the upper surface of the weigh scale. The Karl Fischer titration device is capable of being at least partially inserted into the titration vessel, and the ultrasonic particle detector is capable of being at least partially inserted into the titration vessel. The method includes introducing the hydrocarbon fluid sample into the titration vessel; determining the weight of the hydrocarbon fluid sample in the titration vessel; determining, by the Karl Fischer titration device, the water content of the hydrocarbon fluid sample; and identifying, by the ultrasonic particle detector, the sediment content within the hydrocarbon fluid sample in the titration vessel.

Also provided herein is an integrated Karl Fischer-ultrasonic particle detector device (KF-UPD device). The KF- UPD device includes a weigh scale, a Karl Fischer titration device, a titration vessel, and an ultrasonic particle detector. The titration vessel is in contact with upper surface of the weigh scale. The Karl Fischer titration device is capable of being at least partially inserted into the titration vessel. The ultrasonic particle detector is capable of being at least partially inserted into the titration vessel.

The Karl-Fischer titration device can include a generator electrode for generating $I_2$ and an indicator electrode for measuring electrical current.

The titration vessel can include a lid. The lid can include a surface that defines a first aperture, a second aperture, and a third aperture. The generator electrode can extend at least partially into the titration vessel through the first aperture. The indicator electrode can extend at least partially into the vessel through the second aperture. The ultrasonic particle detector can extend at least partially into the titration vessel through the third aperture.

The weigh scale can be an analytical balance. In some embodiments, the weigh scale includes a weigh scale tray.

The lid can include an injection cap that includes a septum.

In some embodiments, the surface of the lid further defines a fourth aperture and an insertion mixer can extend at least partially into the titration vessel through the fourth aperture. The surface of the lid can further defines a fifth aperture and a solvent fill and solvent waste probe can extend at least partially into the titration vessel through the fifth aperture. The solvent fill and solvent waste probe can include a solvent fill line and a solvent waste line, and the solvent fill line and solvent waste line can extend at least partially into the titration vessel.

In some embodiments, the first aperture is surrounded by a first probe seal that includes a material that is essentially frictionless with regard to the generator electrode. The second aperture can also be surrounded by a second probe seal that includes a material that is essentially frictionless with regard to the indicator electrode. The third aperture can also be surrounded by a third probe seal that includes a material that is essentially frictionless with regard to the ultrasonic particle detector. For example, the first, second, and third probe seals can be ferrofluidic seals.

In some embodiments, the weigh scale, Karl Fischer titration device, titration vessel, and ultrasonic particle detector are enclosed within a housing support unit. The top surface of the housing support unit can define a first, second, and third aperture that correspond to the first, second, and third apertures of the titration vessel, respectively. The generator electrode, indicator electrode, and ultrasonic particle detector can extend at least partially through the corresponding first, second, and third apertures of the housing support unit. The top surface of the housing support unit can further define a fourth aperture that corresponds to the fourth aperture of the titration vessel. The insertion mixer can extend at least partially through the fourth aperture of the top surface of the housing support unit. The top surface of the housing support unit can further define a fifth aperture that corresponds to the fifth aperture of the titration vessel. The solvent fill and solvent waste probe at least partially through the fifth aperture of the top surface of the housing support unit.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Disclosed herein are methods for determining water and sediment content in a hydrocarbon fluid sample. Further disclosed herein are devices for determining water and sediment content in a hydrocarbon fluid sample.

Figure 1A:
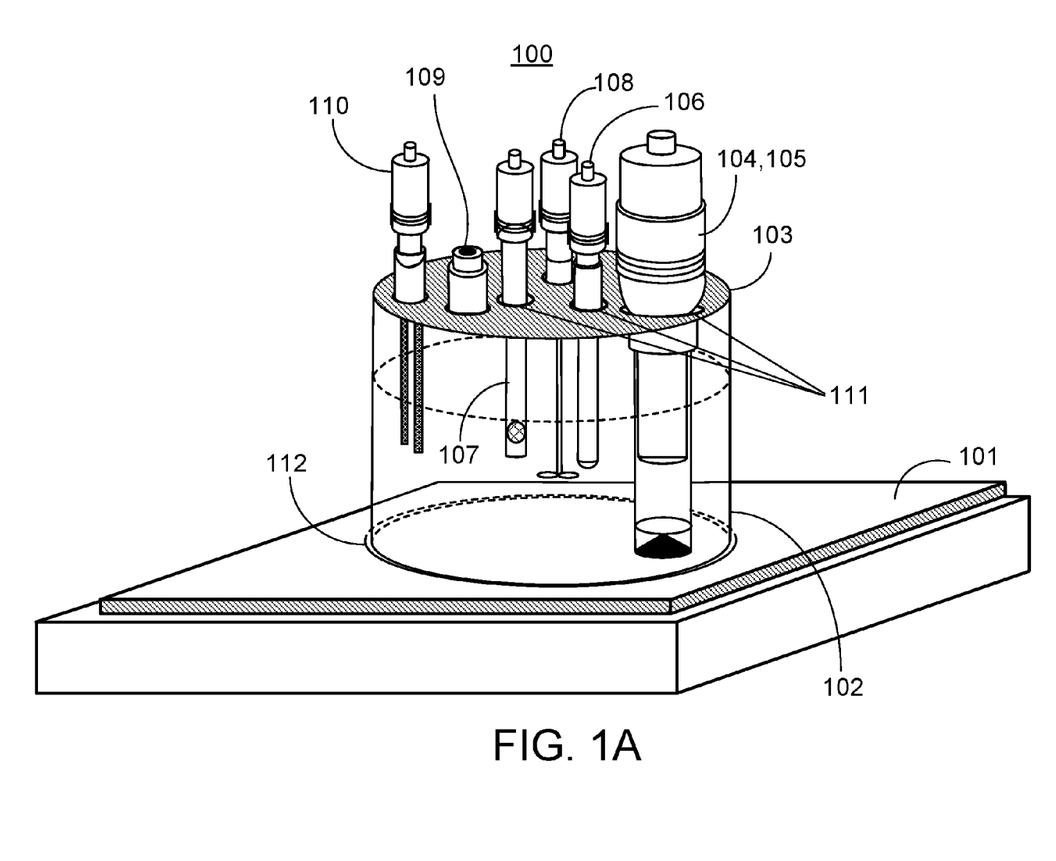
FIG. 1A shows a side view illustrating one embodiment of an integrated Karl Fischer-Ultrasonic Particle Detector device (KF-UPD device), 100, as described in this disclosure.
Figure 1B:
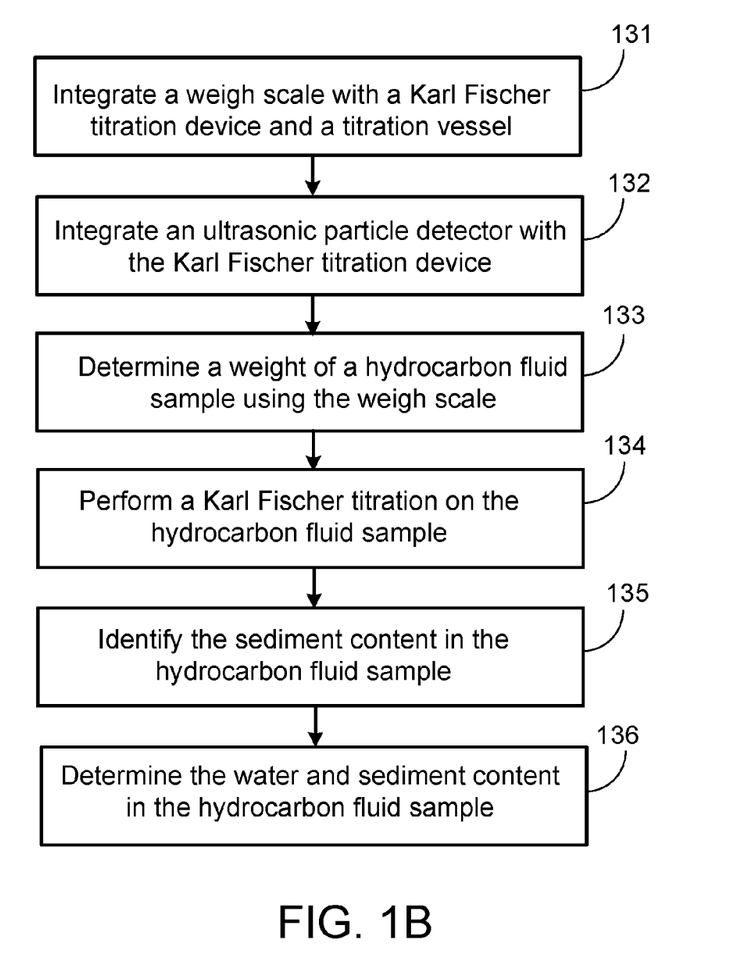
FIG. 1B shows one or more methods for analyzing water and sediment in hydrocarbon fluid samples using an integrated Karl Fischer-Ultrasonic Particle Detector device (KF-UPD device), as described in this disclosure.

Discussion of an embodiment of a method of the present disclosure will now be made with reference to FIG. 1A, which is a side view illustrating one embodiment of an integrated KF-UPD device, 100, as described herein; and with reference to the flow chart of FIG. 1B, which includes methods of determining sediment and water content in a hydrocarbon fluid sample. The hydrocarbon fluid sample can be a sample taken from crude oil.

At block 131 (i) a weigh scale 101, (ii) a Karl Fischer titration device including a generator electrode 104, a drier tube 105, and an indicator electrode 106, (iii) and a titration vessel 102 are integrated such that weigh scale 101 is capable of obtaining the mass of a hydrocarbon fluid sample placed in titration vessel 102 and the Karl Fischer titration device is capable of performing a Karl Fischer titration on a hydrocarbon fluid placed in the titration vessel 102. The weigh scale 101 can be an analytical balance. The balance can have a resolution of 0.1 milligrams (mg) and be capable of determining a weight of over 520 grams. For example, the analytical balance can be a Satorius Cubis® Precision Balance series analytical balance.

The titration vessel 102 can be placed on a weigh scale tray 112. Further, the titration vessel 102 can be placed on a predetermined position of the weigh scale tray 112, by employing corresponding grooves on the titration vessel 102 and weigh scale 112 or by employing a pin mechanism. The titration vessel 102 can be colored or opaque to prevent light-initiated reactions of the Karl-Fischer reagents. For example, the titration vessel 102 can be made of brown glass or plastic. Furthermore, the walls of the titration vessel 102 can be sloped inward. Sloping the walls of the titration vessel inward can ensuring a rounded internal path during fluid circulation to prevent the collection of sediment in the vessel. The titration vessel 102 can include a lid 103, which can be part of the vessel (that is, it cannot be removed) or the lid 103 can be removable (for example, capable of being screwed on or off) or partly removable (for example, capable of being tilted for opening). For example, the lid 103 can be secured to the top of the titration vessel 102 by screwing the lid onto the vessel. The lid 103 can contain ports (for example, openings) through which various devices, such as the generator electrode 104, may be inserted at least partially through. For example, the ports can allow various devices to be vertically inserted though the lid 103 and into a hydrocarbon fluid sample.

The integrated KF-UPD device 100 further includes a generator electrode 104, which is at least partially inserted into the titration vessel through a port in the titration vessels lid 103. The generator electrode 104 can include a cathode cell, which contains a cathode solution such as HYDRANAL-Coulomat CG® or HYDRANAL-Coulomat E®. The generator electrode oxidizes two iodine anions ($I^-$) to form molecular iodine ($I_2$) and two electrons ($e^-$).

$$I^- \rightarrow I_2 + 2e^-$$

Integrated with the generator can be a drier tube 105, which can prevent atmospheric moisture from reacting with the cathode reagents. The integrated KF-UPD device 100 further includes an indicator electrode 106, which is at least partially inserted into the titration vessel through a port in the titration vessel lid 103. The indicator electrode 106 can measure electrical current and, thus, identify the end point of the Karl Fischer titration.

The lid 103 of the titration vessel 102 can also include injection cap 109 that allows the hydrocarbon fluid sample to be placed in the titration vessel 102. The injection cap 109 can be screwed into a port in the titration vessel 102. The top of the injection cap 109 can have internal screw threads to allow insertion of a septum. The injection cap 109 can create a vapor-proof seal to prevent moisture from entering the titration vessel 102.

The integrated KF-UPD device 100 can also include a mixer, such as insertion mixer 108, for mixing the hydrocarbon fluid sample in the titration vessel 102. For example, the lid 103 of the titration vessel 102 can include a port through which insertion mixer 108 can be extended at least partially into the titration vessel 102. The insertion mixer 108 can be a laboratory shear mixer or a propeller-type circulator. The integrated KF-UPD device 100 can also include a solvent refill and waste removal probe 110, which can be at least partially inserted into the titration vessel 102 through a port in the titration vessel's lid 103. The solvent refill and waste removal probe 110 can be used for filling and draining the titration vessel 102. The solvent refill and waste removal probe 110 can be part of a commercially available unit, such as a Mettler Toledo® Solvent Manager.

In some embodiments, the Karl Fischer titration device of integrated KF-UPD device 100 meets the requirements of Chapter 10.9 of the American Petroleum Institute's Manual of Petroleum Measurement Standards (API MPMS). The Karl Fischer titration device can include a generation electrode 104 for generating $I_2$, and the generation electrode can extend at least partially into the titration vessel. The generation electrode can be integrated with drying tube 105. The Karl Fischer device can also include indicator electrode 107 for measuring electrical current, and the indicator electrode can extend at least partially into the titration vessel. In some embodiments, indicator electrode 106 is a double platinum indicator electrode.

Figure 3:
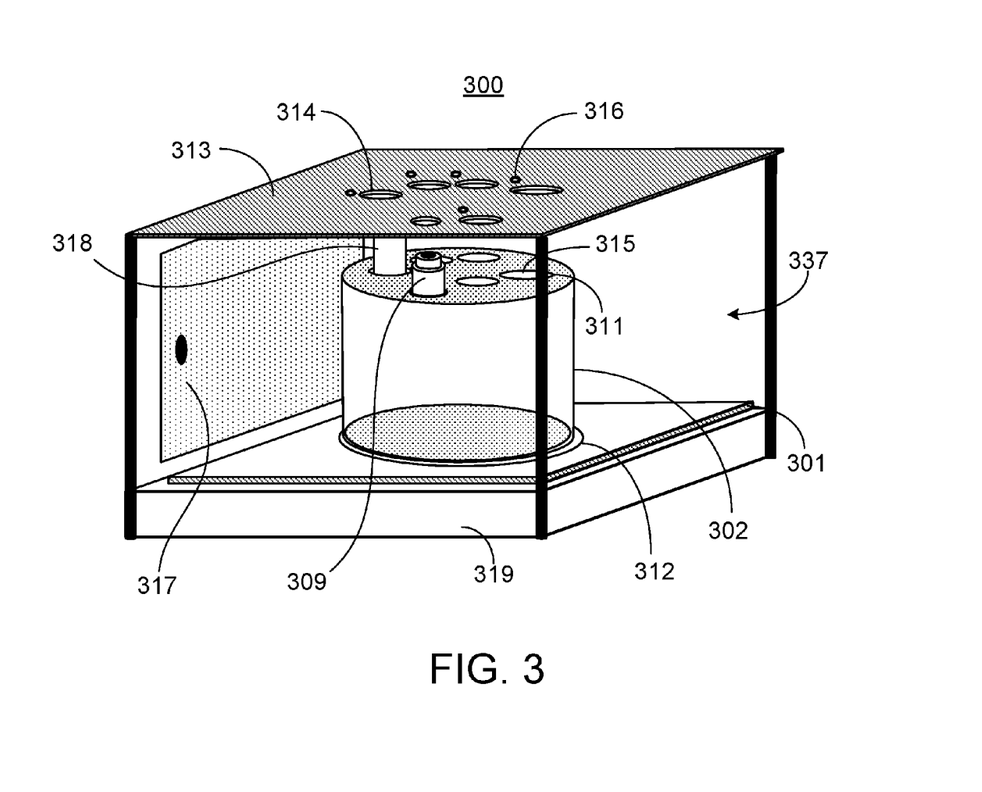
FIG. 3 shows a side view illustrating one embodiment of a partially assembled integrated KF-UPD device, as described in this disclosure.

At block 132 an ultrasonic particle detector 107 is integrated with the weigh scale 101, titration vessel 102, and the Karl Fischer titration device to give integrated KF-UPD device 100. The ultrasonic particle detector 107 is at least partially inserted into the titration vessel 102 through a port in the titration vessel lid 103. The ultrasonic particle detector can detect the presence of various types of materials in the titration vessel 102, such as sediment and paraffinic materials. Furthermore, the integrated KF-UPD device 100 can be housed within a housing support unit (for example, as shown in FIG. 3). The housing support unit can have ports that correspond to the ports in the titration vessel lid that allow the generator electrode, indicator electrode, ultrasonic particle detector, and, optionally, the solvent fill and waste line or lines, and the insertion mixer to extend through the housing support unit. The housing support unit can have a port that corresponds to the location of the injection port. A desiccant can placed within the housing support unit to remove atmospheric moisture from within the housing support unit.

Probe seals 111 can be used to prevent the exchange of atmosphere between the interior of titration vessel 102 and the exterior of the vessel. For example, probe seals 111 can be formed by placing a magnetically permeable sleeve on the outside of the generator electrode 104 and drier tube 105; indicator electrode 106; ultrasonic particle detector 107; insertion mixer 108; and solvent refill and waste removal probe 110, leaving a small gap between the probes and, subsequently, filling the gap with a ferrofuid (for example, by using a syringe).

The weight of a hydrocarbon fluid sample is determined using the weigh scale 101 of the integrated KF-UPD device at block 133. To accomplish this, weigh scale 101 can first be tared and, subsequently, a hydrocarbon fluid sample can be injected into the titration vessel through injection cap 109 of the titration vessel. The weight of the hydrocarbon fluid sample is then determined by weigh scale 101.

A Karl Fischer titration is then performed at block 104. In general, a Karl Fischer titration determines the water content in a liquid or solid. The present method utilizes a cathode solution within the generator electrode 104 and an anode solution contained within the titration vessel 102. The cathode solution can include reagents that can be reduced at the cathode. The anode solution can contain an alcohol, a base, sulfur dioxide ($SO_2$), $I^-$, and, optionally, additional organic solvents. The alcohol can include methanol, ethanol, diethylene glycol monomethyl ether ($CH_3OCH_2CH_2OCH_2CH_2OH$), or combinations thereof. The anode solution can also include HYDRANAL®-Coulomat A, AG, AG-H or E. The volume of anode solution can be higher than the level of cathode solution to reduce instrument drift. The base can include pyridine, imidazole, diethanolamine, or combinations thereof. The organic solvent can include chloroform, formamide, toluene, xylene, or combinations thereof. The organic solvent can also be a commercially available solvent such as Hydranal® Composite 5K or Hydranal® Working Medium K. The optional organic solvent can serve to solubilize any paraffins in the hydrocarbon fluid sample. The Karl Fischer titration utilizes a reaction in which the water in a sample is reacted with a solution of iodine, an alcohol, sulfur dioxide, and an organic base (for example, imidazole or pyridine) to form an alkylsulfite intermediate as shown in Equation 1:

$$CH_3OH + SO_2 + RN \leftrightarrow [RNH]SO_3CH_3 \qquad \text{Eq. 1:}$$

In the next reaction of the Karl Fischer titration, the alkylsulfite reacts with iodine ($I_2$) and the water from the sample (for example, the hydrocarbon fluid sample) as shown in Equation 2:

$$[RNH]SO_3CH_3 + I_2 + H_2O + 2RN \leftrightarrow [RNH]SO_4CH_3 2[RNH]I \quad \text{Eq. 2}$$

In Equation 2, sulfur is oxidized from an alkylsulfite (oxidation number +4) to an alkylsulfate (oxidation number +6) and, further, iodine is reduced as shown in Equations 3 and 4, respectively:

$$SO_3CH_3^{-2} \rightarrow SO_4CH_3^{-2} + 2e- \quad \text{Eq. 3}$$

$$I_2 + 2e^- \rightarrow 2I^- (E^0 = 0.54 \text{ V}) \quad \text{Eq. 4}$$

The reduction of iodine consumes the electrons generated by the oxidation of sulfur, which changes the electrical potential of the system. The changes in potential can be detected by an electrode such as indicator electrode 106, which can be a double platinum electrode. Bipotentiometric measurement can be used to measure the amount of $I_2$ consumed by the water and, thus, to detect the end point of the Karl Fischer titration. Bipotentiometric measurement involves measuring the extent of the reaction by measuring changes in electrical conductivity of the reaction solution. For example, the indicator electrode 106 of the integrated KF-UPD device 100 can maintain a constant current (for example, 5 µA or 10 µA) between the two detector electrodes while measuring the voltage needed to sustain the current. Prior to the end-point, the solution contains $I^-$ and little $I_2$, which is consumed in the reaction (Eq. 2). To maintain the current, the potential must be negative enough to reduce a component of the solvent system. At the equivalence point, excess $I_2$ can accumulate and the current can be carried at a very low voltage, and the abrupt voltage drop indicates the end point. During the Karl Fischer Titration, the insertion mixer can stir the hydrocarbon fluid sample to increase homogeneity of the hydrocarbon fluid sample and, consequently, increase the accuracy of the titration. At the end of the Karl Fischer titration the mass of the water can be reported as a percentage of the hydrocarbon fluid sample.

The sediment content of the hydrocarbon fluid sample is determined at block 105. The sediment content of the hydrocarbon fluid sample can be determined using the ultrasonic particle detector 107 of the integrated KF-UPD device 100. The ultrasonic particle detector 107 sends ultrasonic pulses into the hydrocarbon fluid. When the acoustic pulses hits a particle in the hydrocarbon fluid sample, a part of this ultrasonic energy can be reflected as an echo. The quantity and intensity of these echoes cab be detected, evaluated, and shown as measurement values. As shown in Table 1 and Table 2, there is a difference in the speed of sound in sediment as compared to other materials and fluids.

TABLE 1

| Solids | | | | |
|---|---|---|---|---|
| Substance | Density (g/cm³) | $V_l$ (m/s) | $V_s$ (m/s) | $V_{ext}$ (m/s) |
| Fused silica | 2.2 | 5968 | 3764 | 5760 |
| Glass, pyrex | 2.32 | 5640 | 3280 | 5170 |
| Brick | 1.8 | | | 3650 |
| Clay Rock | 2.2 | | | 3480 |
| Marble | 2.6 | | | 3810 |
| Paraffin | 0.9 | | | 1300 |

TABLE 2

| Liquids | | | | |
|---|---|---|---|---|
| Substance | Formula | Density (g/cm³) | Velocity at 25° C. (m/s) | $-\delta v/-\delta t$ (m/sec ° C.) |
| Acetone | $C_3H_6O$ | 0.79 | 1174 | 4.5 |
| Benzene | $C_6H_6$ | 0.870 | 1295 | 4.65 |
| Carbon tetrachloride | $CCl_4$ | 1.595 | 926 | 2.7 |
| Castor oil | $C_{11}H_{10}O_{10}$ | 0969 | 1477 | 3.6 |
| Chloroform | $CHCl_3$ | 1.49 | 987 | 3.4 |
| Ethanol amide | $C_2H_7NO$ | 1.018 | 1724 | 3.4 |
| Ethyl ether | $C_4H_{10}O$ | 0.713 | 985 | 4.87 |
| Ethylene glycol | $C_2H_6O_2$ | 1.113 | 1658 | 2.1 |
| Glycerol | $C_3H_8O_3$ | 1.26 | 1904 | 2.2 |
| Kerosene | | 0.81 | 1324 | 3.6 |
| Mercury | Hg | 13.5 | 1450 | |
| Methanol | $CH_4O$ | 0791 | 1103 | 3.2 |
| Turpentine | | 0.88 | 1255 | |
| Water (distilled) | $H_2O$ | 0.998 | 1496.7 | -2.4 |

The mass percent of the sediment particles in the hydrocarbon fluid sample can be reported.

The ultrasonic particle detector 107 can also determine and monitor the sediment content of the hydrocarbon fluid sample prior to, and during, the Karl Fischer titration.

At block 106, the water and sediment content of the hydrocarbon sample is determined. The two values can be reported individually or the mass of water and the mass of the sediment content can be totaled and the mass percent of water and sediment can be reported as total mass percent of the hydrocarbon fluid sample.

After the water and sediment content of the hydrocarbon sample is determined, a new hydrocarbon fluid sample can be placed into the titration vessel 102 through the injection cap 109 and the method repeated to determine the water and sediment content of the new hydrocarbon fluid sample. The method may be continuously repeated with additional new hydrocarbon fluid samples. If the overall fluid level in the titration vessel is too high the solvent refill and waste removal probe can be used to remove the desired amount of fluid. Further, if the level of anode solvent in the titration vessel reaches a low level, additional anode solvent can be added through solvent refill and waste removal probe.

Figure 2:
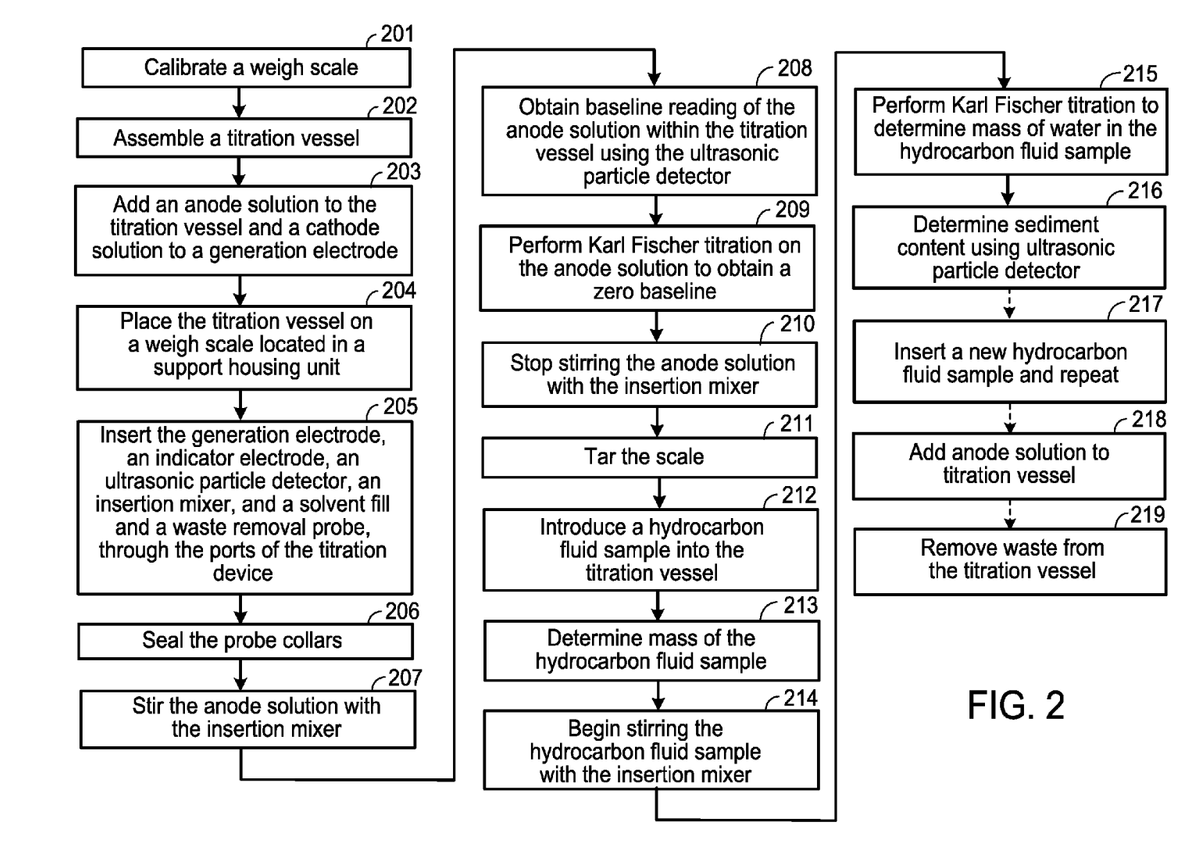
FIG. 2 shows one or more methods for analyzing water and sediment in hydrocarbon fluid samples using an integrated KF-UPD device, as described in this disclosure

Discussion of an embodiment of a method of the present disclosure will now be made with reference to the flow chart of FIG. 2, which includes a method of determining sediment and water content in a hydrocarbon fluid sample using an integrated KF-UDP device, as described herein. At block 201, a weigh scale is calibrated. In some embodiments, the weigh scale is an analytical balance. For example, the balance can have a resolution of 0.1 mg and be capable of determining a weight of over 520 grams. At block 202, the titration vessel is assembled. Assembling the titration vessel can include placing and securing a lid on the titration vessel, if the lid is removable (for example, capable of being screwed on and off). At block 203, anode solution is added to the titration vessel and cathode solution is added to a generation electrode. In some embodiments, the anode solution is added to the titration vessel before a removable lid is secured on the top of the titration vessel.

At block 204, the titration vessel is placed on a weigh scale located in a support housing unit. Placing the titration vessel on a weigh scale can include securing the titration vessel on a weigh scale tray—which is located on the top of the weigh scale. For example, the titration vessel can be secured on the weigh scale tray by using a pin assembly or corresponding molded grooves. In some embodiments, the weigh scale tray and titration vessel have corresponding molded groves that allow for the titration vessel to be placed on a designated location of the weigh scale. Securing the titration vessel on a designated location on the weigh scale tray can ensure that the ports of the titration vessel lid align with the corresponding ports of a housing support unit.

At block 205, a generation electrode, an indicator electrode, an ultrasonic particle detector, an insertion mixer, and a solvent fill and a waste removal probe are inserted through the ports of the housing support unit and the corresponding ports of the titration device. The probe seals are then sealed at block 206. Sealing the probe seals can include injecting a ferromagnetic fluid into the space between the probe seals including a magnetic assembly and the apparatus inserted into the port. The ferromagnetic fluid can be placed into the space between the probe seal and the apparatus (for example, the generator electrode) by inserting a needle of a syringe into seal injection holes of the housing support unit and, subsequently, placing the ferromagnetic fluid into the space between the probe seal and the apparatus.

The anode solution is stirred with the insertion mixer at block 207. The speed of the insertion mixer can be adjusted such that a vortex is present and no bubbles are formed in the anode solution. At block 208, a baseline reading of the anode solution within the titration vessel is obtained using the ultrasonic particle detector (208). Subsequently, at block 209 a Karl Fischer titration is performed on the anode solution to remove any residual water and to obtain a zero baseline. After the end point of the Karl Fischer titration has been reached, the stirring of the anode solution is stopped at block 210. In some embodiments, Karl Fischer titration quality control standards are performed prior to stopping stirring of the anode solution. At block 211 the weigh scale is tared.

At block 212 a hydrocarbon fluid sample is introduced into the titration vessel. The hydrocarbon fluid can be introduced directly into the titration vessel through the injection cap in the titration vessel and the corresponding port in the support housing unit. For example, a syringe can be used to enter and extend through the septum of the injection cap of the titration vessel and insert the hydrocarbon fluid sample below the level of the anode solvent. Subsequently, the mass of the hydrocarbon fluid is determined at block 213.

At block 214, stirring of the hydrocarbon fluid sample begins. Simultaneously, or subsequently, at block 215 a Karl Fischer titration is performed to determine the mass of the water in the hydrocarbon fluid sample. After the end point of the titration is reached, at block 216, the sediment content of the hydrocarbon fluid sample is determined using the ultrasonic particle detector.

At block 217, optionally, an additional hydrocarbon fluid sample is inserted and the steps at blocks 212 through block 216 are repeated.

At block 218, optionally, additional anode solution is added to the titration vessel. For example, additional anode solution can be added via the solvent refill and waste removal probe, a solvent pump, and a reservoir that contains anode solution.

At block 219, optionally, waste is removed from the titration vessel. For example, waste can be removed from the titration vessel via the solvent fill and waste removal probe and a waste removal pump, which transfers the waste to a waste reservoir.

Referring to FIG. 3, a side view illustrates one embodiment of a partially assembled integrated KF-UPD device 300, as described herein. The integrated KF-UPD device 300 includes a weigh scale 301, such as an analytical balance. The integrated KF-UPD device 300 also includes a titration vessel 302, which is placed on a weigh scale tray 312. The titration vessel 302 contains an injection cap 309. The titration vessel 302 contains probe seals 311. The weigh scale 301 and titration vessel 302 are enclosed in a housing support unit 313. The housing support unit includes a base 319. The housing support unit 313 includes ports 314 that correspond to the vessel ports 315. The housing support unit 313 also includes seal injection ports 316. The seal injection ports 316 can have a diameter large enough such that a needle of a syringe can pass through the seal injection ports 316 and be used to inject a ferrofluid into the probe seals 311. The housing support unit 313 further includes an access door 317. The partially assembled integrated KF-UPD device 300 also include a drier tube 318. The drier tube 318 can absorb atmospheric moisture content in the housing unit.

Figure 4:
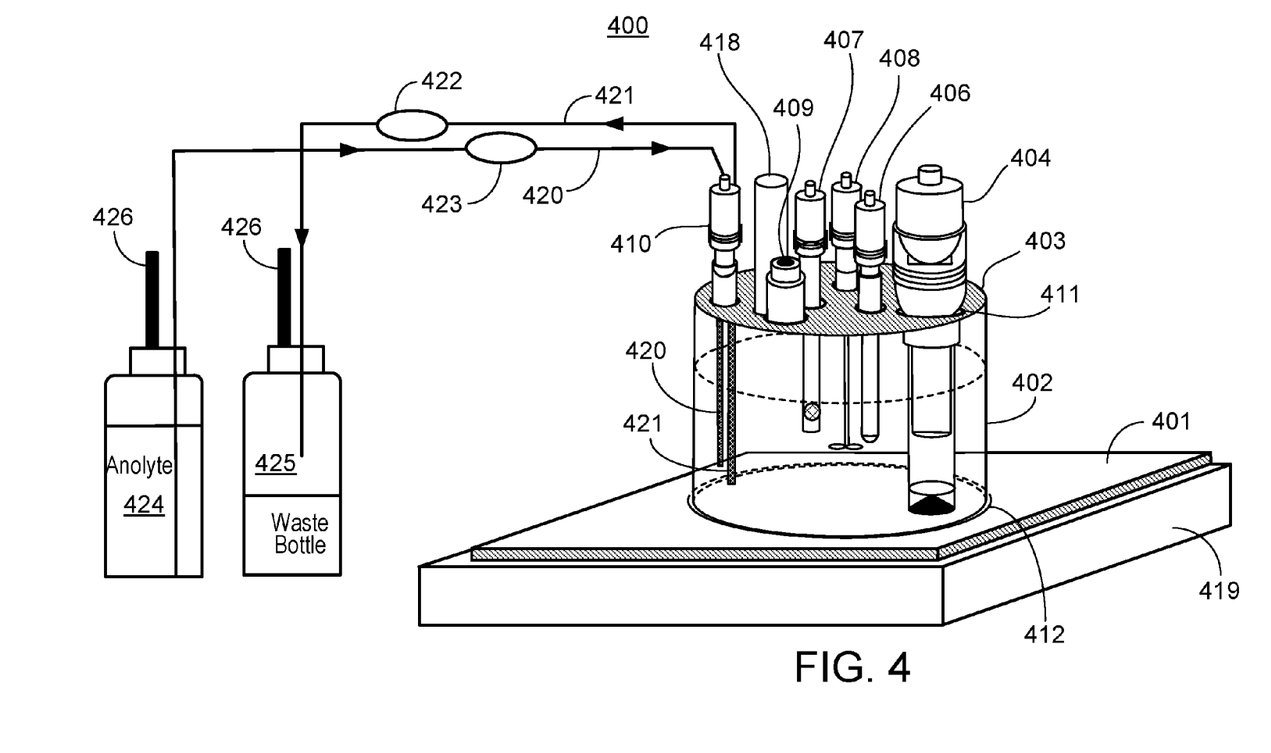
FIG. 4 shows a side view illustrating one embodiment of an integrated KF-UPD device that includes a waste removal and solvent refill system, as described in this disclosure.

Referring to FIG. 4, a side view illustrates one embodiment of an integrated KF-UPD device 400 that includes a waste removal and solvent refill system. KF-UPD device 400 includes weigh scale 401, which is located on top of the housing unit base 419. On top of the weigh scale is weigh scale tray 412 on which the titration vessel 402 is located. The titration vessel 402 includes lid 403, which includes ports (for example, openings) through which various apparatuses are inserted into the titration vessel 402 such that the apparatuses extend at least partially into the titration vessel 402. For example, inserted through the ports in lid 403 are generator electrode 404, indicator electrode 406, insertion mixer 408, ultrasonic particle detector 407, drier tube 418, and the solvent refill and waste removal probe 410. Lid 403 also includes injection cap 409.

The solvent refill and waste removal probe 410 includes solvent line 420 and waste line 421. Solvent line 420 is connected to, and inserted at least partially into solvent reservoir 424. Solvent pump 423 is located along the path of solvent line 420 and between the solvent probe and waste removal probe 410 and the solvent reservoir 424. Solvent pump 423 is capable of transferring solvent from the solvent reservoir 424 to the titration vessel 402. In some embodiments, solvent reservoir 424 is filled with an anode solvent and solvent pump 423 transfers anode solvent from the solvent reservoir 424 to the titration vessel 403 when needed. Waste line 421 is connected to, and inserted at least partially into waste reservoir 425. Waste pump 422 is located along the path of waste line 421 and between the solvent probe 410 and the waste reservoir 425. Solvent pump 422 is capable of transferring waste from the titration vessel 402 to the waste reservoir 425. Solvent reservoir 424 and waste reservoir 424 contain drier tubes 426. Drier tubes 426 can prevent atmospheric moisture from reacting with the reagents through the vent port.

Figure 5A:
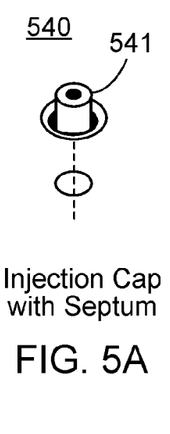
FIG. 5A-5F shows a side view, of an injection cap with a septum (FIG. 5A), an indicator electrode (FIG. 5B), a generator electrode and drying port (FIG. 5C), a solvent fill and waste line (FIG. 5D), an insertion mixer (FIG. 5E), and an ultrasonic particle detector (FIG. 5F), as described in this disclosure.
Figure 5B:
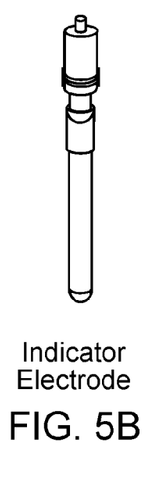
Figure 5C:
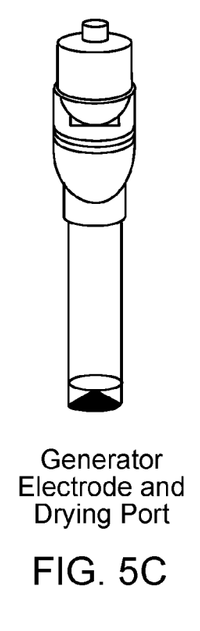
Figure 5D:
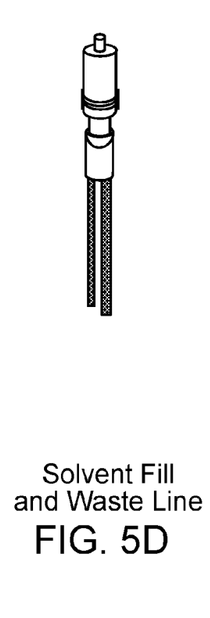
Figure 5E:
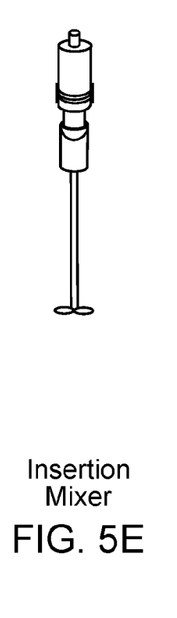
Figure 5F:
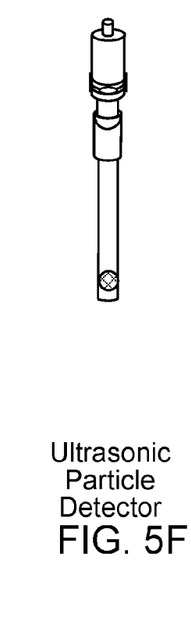

Referring to FIG. 5A-5F, a side view, illustrates embodiments of an injection cap 540 with a septum 541 (FIG. 5A), an indicator electrode (FIG. 5B), a generator electrode and drying port (FIG. 5C), a solvent fill and waste line (FIG. 5D), an insertion mixer (FIG. 5E), and an ultrasonic particle detector (FIG. 5F).

Figure 6:
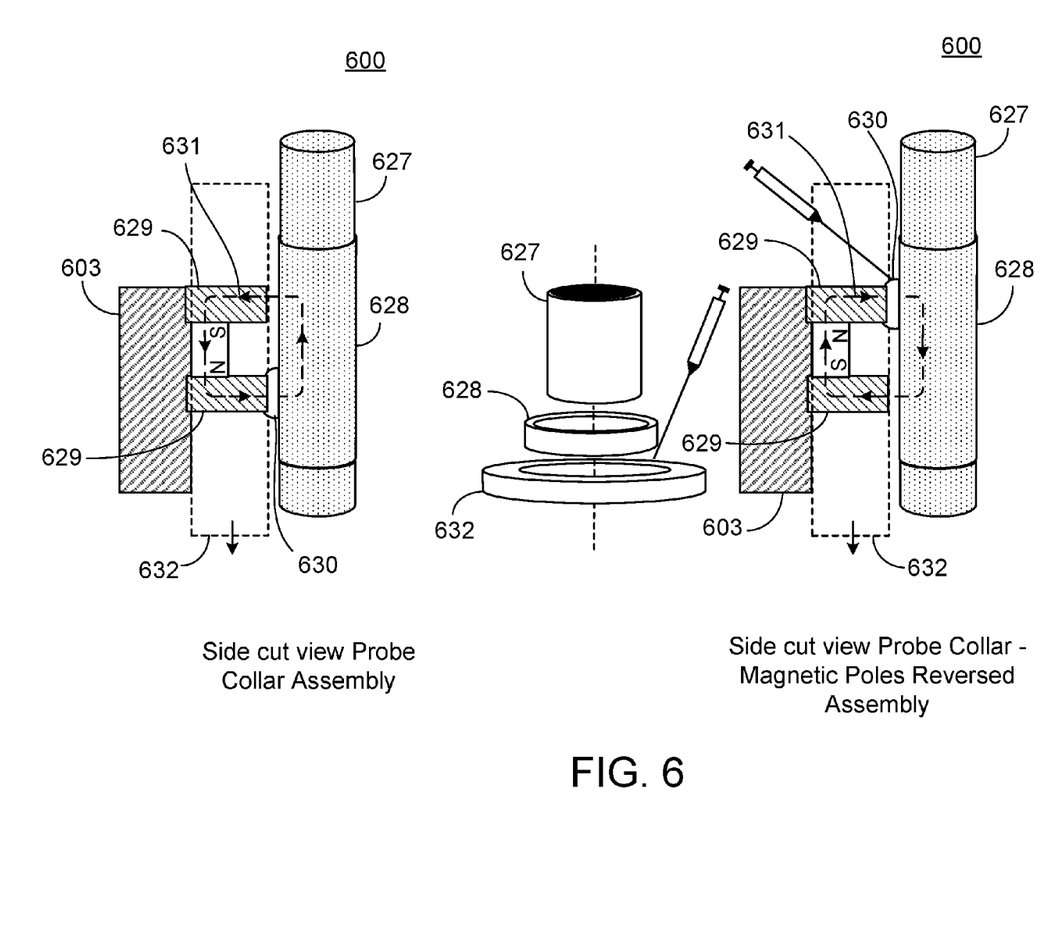
FIG. 6 shows two side views of a ferromagnetic fluid probe seal, as described in this disclosure.

As discussed in this disclosure, a probe seal can seal the space between a probe (for example, a generator electrode) and the lid of a titration vessel. For example, a ferromagnetic probe seal can be used as a probe seal. Referring to FIG. 6, a side view illustrates one embodiment of a ferromagnetic probe seal 600 as described herein. Ferromagnetic probe seal 600 includes the magnet assembly 632 and ferromagnetic fluid 630. The magnet assembly 632 occupies a circumferential portion of the opening a port in the lid 603 of a titration vessel. Magnet assembly 632 can be in contact with the lid 603. Magnet assembly 632 includes pole pieces 629. The pole pieces 629 generate a magnetic flux 631, which holds in place ferromagnetic fluid 630. Ferromagnetic fluid 630 can be in direct contact with the probe shaft 627 of a probe (for example, a generator electrode) or ferromagnetic fluid 630 can be in contact with a magnetically permeable collar 628, which is in contact with probe shaft 627.

Figure 7:
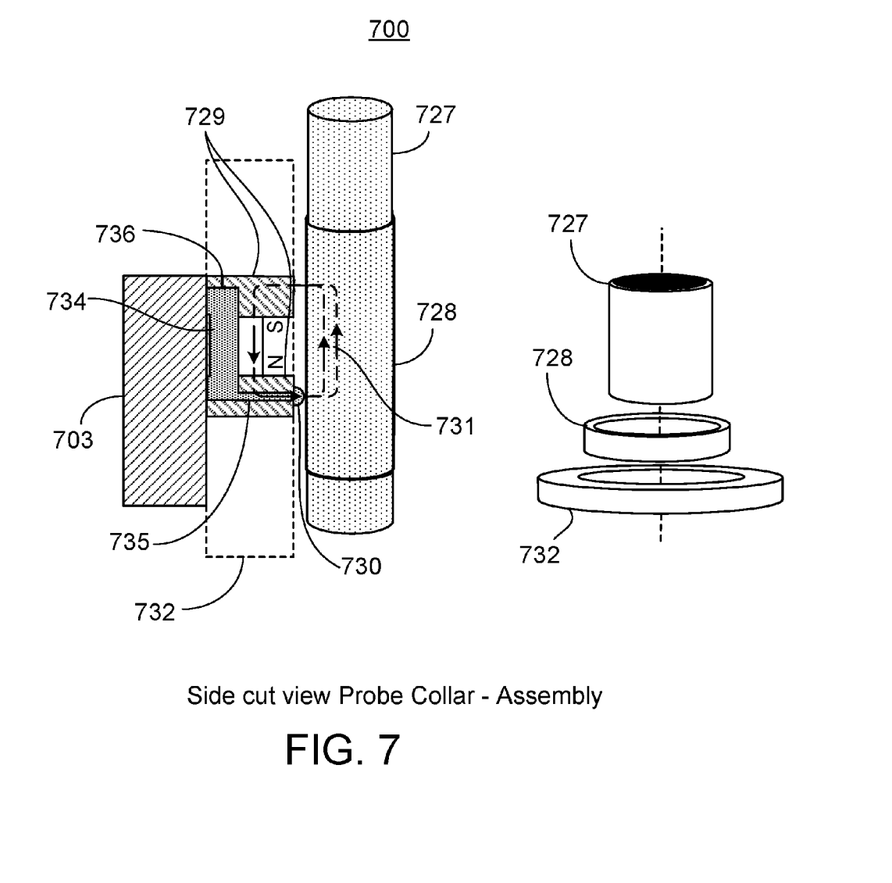
FIG. 7 shows a side views of a ferromagnetic fluid probe seal with an integrated ferromagnetic fluid reservoir, as described in this disclosure.

Referring to FIG. 7, a side view illustrates one embodiment of a ferromagnetic probe seal 700 as described herein. Ferromagnetic probe seal 700 includes the magnet assembly 732 and ferromagnetic fluid 730. The magnet assembly 732 occupies a circumferential portion of the opening of a port in the lid 703 of a titration vessel. Magnet assembly 732 can be in contact with lid 703. Magnet assembly 732 includes pole pieces 729. The pole pieces 729 generate a magnetic flux 731, which holds in place ferromagnetic fluid 730. Ferromagnetic fluid 730 can be in direct contact with the probe shaft 727 of a probe (for example, a generator electrode) or ferromagnetic fluid 730 can be in contact with a magnetically permeable collar 728, which is in contact with probe shaft 727. The magnet assembly includes reservoir 734. Reservoir 734 can be filled with a ferromagnetic fluid. The magnet assembly 732 includes ferromagnetic fluid exit line 735. Ferrofluid exit line 735 is configured to allow a ferromagnetic fluid to move from the reservoir 734 to the open space between the magnet assembly 732 and probe shaft 727. The magnet assembly 732 includes fill/vent line 736. Fill/vent line 736 is configured to allow a ferromagnetic fluid to be injected into reservoir 734 and to allow a ferromagnetic fluid to exit reservoir 734. Increased pressure in reservoir 734 can lead to a ferromagnetic fluid exiting reservoir 734 through fill/vent line 736.

A number of embodiments of the subject matter have been described. Other aspects, advantages, and modifications are within the scope of the following claims.

What is claimed is:

1. A method for determining water and sediment content in a hydrocarbon fluid sample, the method comprising:
   integrating a weigh scale with a Karl Fischer titration device and a titration vessel configured to implement a Karl Fischer titration method;
   integrating an ultrasonic particle detector with the Karl Fischer titration device, the ultrasonic particle detector configured to identify sediment in the hydrocarbon fluid sample;
   determining, by the weigh scale, the weight of the hydrocarbon fluid sample;
   performing, by the Karl Fischer titration device, the Karl Fischer titration method on the hydrocarbon fluid sample to determine the water content in the hydrocarbon fluid sample; and
   identifying, by the ultrasonic particle detector, the sediment content in the hydrocarbon fluid sample.

2. The method of claim 1, wherein the Karl Fischer titration device comprises (i) a generator electrode for generating $I_2$, wherein the generator electrode extends at least partially into the titration vessel and (ii) an indicator electrode for measuring electrical current, wherein the indicator electrode extends at least partially into the titration vessel,
   wherein the Karl Fischer titration is performed using the generator electrode and indicator electrode.

3. The method of claim 2, wherein the titration vessel comprises a lid, wherein the lid comprises a surface that defines a first aperture, a second aperture, and a third aperture, and wherein (i) the generator electrode for generating $I_2$ extends at least partially into the titration vessel through the first aperture; (ii) the indicator electrode for measuring electrical current extends at least partially into the titration vessel through the second aperture; and (iii) the ultrasonic particle detector for identifying sediment extends at least partially into the titration vessel through the third aperture.

4. The method of claim 3, wherein the lid further comprises an injection cap comprising a septum and the method further comprises injecting the hydrocarbon sample into the titration vessel through the septum of the injection cap.

5. The method of claim 4, wherein the surface of the lid further defines a fourth aperture and wherein an insertion mixer extends at least partially into the titration vessel through the fourth aperture, wherein the insertion mixer mixes the hydrocarbon fluid.

6. The method of claim 5, wherein the surface of the lid further defines a fifth aperture and wherein a solvent fill line and a solvent waste line extend at least partially into the titration vessel through the fifth aperture.

7. The method of claim 6, wherein the first aperture is surrounded by a first probe seal comprised of a material that is essentially frictionless with regard to the generator electrode, wherein the second aperture is surrounded by a second probe seal that comprised of a material that is essentially frictionless with regard to the indicator electrode, and wherein the third aperture is surrounded by a third probe seal comprised of a material that is essentially frictionless with regard to the ultrasonic particle detector, the first, second, and third probe seals permitting the generator electrode, indicator electrode, and ultrasonic particle detector to move vertically relative to the vessel.

8. The method of claim 7, wherein the first, second, and third probe seals are ferrofluidic seals.

9. The method of claim 2, wherein a cathode solution is contained within the generator electrode.

10. The method of claim 1, further comprising enclosing the weigh scale, the Karl Fischer titration device, the titration vessel, and ultrasonic particle detector within a housing support unit.

11. The method of claim 10, wherein the titration vessel comprises a lid, wherein the lid comprises a surface that defines a first aperture, a second aperture, and a third aperture, and a top surface of the housing support unit defines a first, second, and third aperture that correspond to the first, second, and third apertures defined in the surface of the lid, respectively, and
   wherein a generator electrode, an indicator electrode, and the ultrasonic particle detector extend at least partially through the corresponding first, second, and third apertures of the housing support unit.

12. The method of claim 11, wherein the surface of the lid further defines a fourth aperture and the top surface of the housing support unit further defines a fourth aperture that corresponds to the fourth aperture defined in the surface of the lid, and wherein an insertion mixer extends at least partially through the fourth aperture of the top surface of the housing support unit.

13. The method of claim 12, wherein the surface of the lid further defines a fifth aperture and the top surface of the housing support unit further defines a fifth aperture that corresponds to the fifth aperture defined in the surface of the lid, and wherein a solvent fill line and a solvent waste line extend at least partially through the fifth aperture of the top surface of the housing support unit.

14. The method of claim 1, wherein the weigh scale is an analytical balance.

15. The method of claim 1, wherein the Karl Fischer titration method is a coulometric titration method.

16. The method of claim 1, wherein an anode solution is contained in the titration vessel.

17. A method for determining water and sediment content in a hydrocarbon fluid sample using an integrated Karl Fischer-ultrasonic particle detector device (KF-UPD device), wherein the KF-UPD device comprises a weigh scale, a Karl Fischer titration device, a titration vessel, and an ultrasonic particle detector, wherein the titration vessel is in contact with upper surface of the weigh scale, the Karl Fischer titration device is capable of being at least partially inserted into the titration vessel, and the ultrasonic particle detector is capable of being at least partially inserted into the titration vessel,
the method comprising:
introducing the hydrocarbon fluid sample into the titration vessel;
determining the weight of the hydrocarbon fluid sample in the titration vessel;
determining, by the Karl Fischer titration device, the water content of the hydrocarbon fluid sample; and
identifying, by the ultrasonic particle detector, the sediment content within the hydrocarbon fluid sample in the titration vessel.

18. An integrated Karl Fischer-ultrasonic particle detector device (KF-UPD device), the KF-UPD device comprising:
a weigh scale;
a Karl Fischer titration device;
a titration vessel; and
an ultrasonic particle detector,
wherein the titration vessel is in contact with an upper surface of the weigh scale, the Karl Fischer titration device is capable of being at least partially inserted into the titration vessel, and the ultrasonic particle detector is capable of being at least partially inserted into the titration vessel.

19. The KF-UPD device of claim 18, wherein the Karl-Fischer titration device comprises a generator electrode for generating $I_2$ and an indicator electrode for measuring electrical current.

20. The KF-UPD device of claim 19, wherein the titration vessel comprises a lid, wherein the lid comprises a surface that defines a first aperture, a second aperture, and a third aperture, and wherein (i) the generator electrode extends at least partially into the titration vessel through the first aperture; (ii) the indicator electrode extends at least partially into the titration vessel through the second aperture; and (iii) the ultrasonic particle detector extends at least partially into the titration vessel through the third aperture.

21. The KF-UPD device of claim 20, wherein the lid further comprises an injection cap comprising a septum.

22. The KF-UPD device of claim 21, wherein the surface of the lid further defines a fourth aperture and wherein an insertion mixer extends at least partially into the titration vessel through the fourth aperture.

23. The KF-UPD device of claim 22, wherein the surface of the lid further defines a fifth aperture and wherein a solvent fill and solvent waste probe extends at least partially into the titration vessel through the fifth aperture.

24. The KF-UPD device of claim 23, wherein the solvent fill and solvent waste probe comprises a solvent fill line and a solvent waste line, wherein the solvent fill line and solvent waste line extend at least partially into the titration vessel.

25. The KF-UPD device of claim 24, wherein the first aperture is surrounded by a first probe seal comprised of a material that is essentially frictionless with regard to the generator electrode, wherein the second aperture is surrounded by a second probe seal comprised of a material that is essentially frictionless with regard to the indicator electrode, and wherein the third aperture is surrounded by a third probe seal comprised of a material that is essentially frictionless with regard to the ultrasonic particle detector.

26. The KF-UPD device of claim 25, wherein the weigh scale, the Karl Fischer titration device, the titration vessel, and the ultrasonic particle detector are enclosed within a housing support unit.

* * * * *

UNITED STATES PATENT AND TRADEMARK OFFICE
CERTIFICATE OF CORRECTION

PATENT NO. : 10,067,091 B2
APPLICATION NO. : 15/224136
DATED : September 4, 2018
INVENTOR(S) : James Clyde Hassell, Jr. et al.

It is certified that error appears in the above-identified patent and that said Letters Patent is hereby corrected as shown below:

In the Claims

Column 12, Line 39, Claim 10, after "vessel, and" insert --the--.

Column 14, Line 23, Claim 24, after "line and" insert --the--.

Signed and Sealed this
Twenty-fifth Day of December, 2018

Andrei Iancu
*Director of the United States Patent and Trademark Office*